`US010000816B2`

(12) United States Patent
Kikulska et al.

(10) Patent No.: US 10,000,816 B2
(45) Date of Patent: Jun. 19, 2018

(54) METHOD FOR DETECTING AN INCREASED RISK OF DEVELOPING SKIN CANCER AND A USE OF A GENOTYPE VARIANT OF THE GRHL3 GENE

(71) Applicant: INSTYTUT BIOLOGII DOSWIADCZALNEJ IM. M. NENCKIEGO POLSKIEJ AKADEMII NAUK, Warsaw (PL)

(72) Inventors: Agnieszka Kikulska, Lubawa (PL); Tomasz Michal Wilanowski, Warsaw (PL); Piotr Lukasz Rutkowski, Warsaw (PL)

(73) Assignee: INSTYTUT BIOLOGII DOSWIADCZALNEJ IM. M. NENCKIEGO POLSKIEJ AKADEMII NAUK, Warsaw (PL)

( * ) Notice: Subject to any disclaimer, the term of this patent is extended or adjusted under 35 U.S.C. 154(b) by 0 days. days.

(21) Appl. No.: 15/106,163

(22) PCT Filed: Dec. 19, 2014

(86) PCT No.: PCT/PL2014/050078
§ 371 (c)(1),
(2) Date: Jun. 17, 2016

(87) PCT Pub. No.: WO2015/093998
PCT Pub. Date: Jun. 25, 2015

(65) Prior Publication Data
US 2017/0029897 A1 Feb. 2, 2017

(30) Foreign Application Priority Data

Dec. 19, 2013 (IT) .............................. MI2013A2141
Nov. 3, 2014 (PL) ....................................... 410049

(51) Int. Cl.
*C12Q 1/68* (2006.01)
(52) U.S. Cl.
CPC ......... *C12Q 1/6886* (2013.01); *C12Q 1/6827* (2013.01); *C12Q 2600/118* (2013.01); *C12Q 2600/156* (2013.01)

(58) Field of Classification Search
None
See application file for complete search history.

(56) References Cited

FOREIGN PATENT DOCUMENTS

WO 2013029116 A1 3/2013

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Kikulska et al, FEBS J. 279 (Suppl. 1), 288 (Abstract P13-3) (Aug. 30, 2012).*
Lin et al. "The grainyhead-like 2 gene (GRHL2) single nucleotide polymorphism is not associated with age-related hearing impairment in Han Chinese", The Laryngoscope, vol. 121, Issue 6, pp. 1303-1307, Jun. 2011.
Van Laer et al. "The grainyhead like 2 gene (GRHL2), alias TFCP2L3, is associated with age-related hearing impairment", Human Molecular Genetics, vol. 17, Issue 2, pp. 159-169 (2008).
Peters et al. "Mutation of a transcription factor, TFCP2L3, causes progressive autosomal dominant hearing loss, DFNA28", Human Molecular Genetics, vol. 11, Issue 23, pp. 2877-2885 (2002).
Kamiyama et al."Polymorphisms in the 3' UTR in the neurocalcin σ gene affect mRNA stability, and confer susceptibility to diabetic nephropathy", Human Genetics, Nov. 2007, vol. 122, Issue 3-4, pp. 397-407 (2007).
Bhandari et al. "The Grainyhead transcription factor Grhl3/Get1 suppresses miR-21 expression and tumorigenesis in skin: modulation of the miR-21 target MSH2 by RNA-binding protein DND1" Oncogene 32, 1497-1507 (Mar. 21, 2013).
Darido et al. "Targeting of the Tumor Suppressor GRHL3 by a miR-21-Dependent Proto-Oncogenic Network Results in PTEN Loss and Tumorigenesis" Cancer Cell, vol. 20, Issue 5, 635-648, Nov. 15, 2011.
Panis et al. "Putative circulating markers of the early and advanced stages of breast cancer identified by high-resolution label-free proteomics" Cancer Letters vol. 330, Issue 1 , pp. 57-66, Mar. 1, 2013.
Boglev, et al., "The unique and cooperative roles of the Grainy head-like transcription factors in epidermal development reflect unexpected target gene specificity," Developmental Biology, 349 (2011) 512-522.
Kikulska, et al., "Genetic and epigenetic analysis of GRHL genes in human skin cancers," FEBS Journal, vol. 279, No. Suppl. 1, Sp. Iss. SI, Sep. 2012, p. 88.

* cited by examiner

*Primary Examiner* — James Martinell
(74) *Attorney, Agent, or Firm* — Arrigo, Lee, Guttman & Mouta-Bellum

(57) ABSTRACT

The present invention is directed to methods of identifying SNP markers associated with skin cancers, and use of these markers to explain individual susceptibility to skin cancer development. In addition, described SNPs have been identified as potentially crucial for proper GRHL3 protein function.

16 Claims, 4 Drawing Sheets

PI3K/AKT SIGNALING PATHWAY AND THE GRHL3/PTEN/miR-21 REGULATORY LOOP

ALTERNATIVE SPLICE VARIANTS OF GRHL3 mRNA

Manhattan Plot

Location of the potential phosphorylation site in a schematic of the GRHL3 gene; Kinases potentially recognisisng the amino-acid motif dependent on SNP1 and SNP2

Changes in the expression level of GRHL genes in patients with non-melanoma skin cancer; correlation of the expression of GRHL1 and GRHL3

METHOD FOR DETECTING AN INCREASED RISK OF DEVELOPING SKIN CANCER AND A USE OF A GENOTYPE VARIANT OF THE GRHL3 GENE

This invention relates generally to the field of cancer diagnostics, and in particular to the detection of an increased risk of developing a skin cancer. Specifically, the present invention relates to a method of detecting and identifying an increased risk of developing a skin cancer in a human patient based on polymorphisms of the GRHL3 gene. The present invention is useful in medical diagnostics, and cancer risk screening.

Skin cancer is the most frequent malignant neoplasm, with a constantly increasing incidence and morbidity. According to World Health Organization (WHO), between 2 and 3 million non-melanoma skin cancers and 132,000 melanoma skin cancers occur globally each year. The most common form of skin cancer is non-melanoma skin cancer (NMSC) which comprises basal cell carcinomas (BCC; 75%) and squamous cell carcinomas (SCC; 20%). Melanoma accounts for less than 5% of skin cancer cases, but constitutes the vast majority of skin cancer deaths (14). In contrast to melanoma, NMSCs are rarely lethal. Problems with treatment result from diagnosis at late stages. The symptoms of non-melanoma skin cancer may be similar to symptoms of other non-cancerous skin conditions and may be ignored by patients in early stages. Surgical excision remains the gold standard in the treatment of non-melanoma skin cancers, but this method is painful and often disfiguring, especially when the area of excision is large. Therefore, prevention and early detection as well as treatment strategies are needed. According to WHO, the incidence of skin cancers typically depends on ultraviolet radiation (9). A large number of studies indicate that the risk of malignant melanoma correlates with genetic and personal characteristics, and a person's UV exposure behavior. Likewise, about 90% of non-melanoma skin cancers are associated with exposure to ultraviolet radiation from the sun (4). Several studies have also demonstrated that exposure to environmental levels of UV radiation leads to accumulation of mutations and alters the activity and distribution of the cells responsible for triggering immune responses in humans (5). A relatively new clinical phenomenon is the increasing number of NMSC cases among immunosuppressed patients. It was shown that patients treated with immunosuppressive drugs have a greater incidence of squamous cell carcinoma than the general population (6,7,8).

Genetic variations (that weaken proper function or structure of epidermis and/or proper function of immune system and/or DNA-damage repair process) together with UV-induced DNA damage may increase susceptibility of individuals to skin cancer developing.

Most human skin diseases, including skin cancers, arise from aberrant differentiation or disrupted balance between proliferation and differentiation of keratinocytes in the epidermis. Epidermal differentiation and stratification, crucial for skin barrier formation, are regulated by a complex interplay of transcription factors, including the evolutionarily conserved Grainyhead-like 3 (GRHL3). GRHL3 is known to be involved in the following biological processes: epidermal development; central nervous system development; planar cell polarity pathway involved in neural tube closure; wound healing; regulation of actin cytoskeleton organization and biogenesis; ectoderm development; positive regulation of transcription from RNA polymerase II promoter; pattern specification process; positive regulation of Rho GTPase activity and endothelial cell migration and angiogenesis.

GRHL3 regulates epidermal genes directly by controlling the expression of protein-coding genes (including TGM1 and PTEN) as well as specific microRNAs (miRs), one of which is miR-21, previously shown to be upregulated in skin diseases, including psoriasis and squamous cell skin cancer. MicroRNA-21 is normally expressed in the post-mitotic suprabasal layers of the epidermis, overlapping with GRHL3 (10). Therefore, these two factors are involved in a regulatory loop maintaining homeostasis in the epidermis. Decreased GRHL3 expression contributes to tumor progression and upregulation of the oncomiR-21 in squamous cell carcinoma of the skin. It is known that miRNA-21 targets PTEN and GRHL3 in human cancers. This synchronous targeting of GRHL3 and PTEN by miRNA-21 establishes a proto-oncogenic network with amplification of PI3K/AKT/mTOR signaling and induction of squamous cell carcinoma in humans. The PI3K/AKT pathway is one of the most important signaling networks in cancer. There is growing evidence that activation of this pathway plays also a significant role in melanoma (15). Therefore, GRHL3 transcription factor seems to play an important role of skin tumor suppressor by indirect inhibition of PI3K/AKT pathway. It was shown that loss of GRHL3 results in exclusive upregulation of PI3K/AKT/mTOR signaling. Deletion or inactivation of GRHL3 in adult epidermis evokes loss of expression of PTEN, a direct GRHL3 target, and upregulation of miRNA-21, resulting in activation of PI3K/AKT/mTOR signaling, with a complete loss of ERK phosphorylation and no change in the levels of p-EGFR, and inducing aggressive squamous cell neoplasms (16).

The PI3K/AKT pathway activation seems to be important in both skin cancer initiation and therapeutic resistance. Therefore, identification of Single Nucleotide Polymorphisms (SNPs) in GRHL3 coding sequence may be useful to define individual's resistance to inhibitors against the PI3K-AKT pathway. Experiments on mice have shown that mice subcutaneously injected with transformed keratinocytes lacking Grhl3 exhibit increased tumorigenesis. Moreover, conditionally knockout mice (Grhl3$^{\Delta/-}$/K14Cre+) are much more susceptible to SCC formation upon DMBA/TPA treatment than wild type mice.

Skin cancer occurs when mutations accumulate in the DNA of epidermal cells and balance between proliferation and differentiation is disrupted. Skin cancers are characterized by a significant frequency of ultraviolet-like transition mutations (C→T and CC→TT) in coding sequences of RAS oncogenes, as well as in p53 and PTCH tumor suppressor genes (11). Somatic mutations, linked to skin cancers, have been found in XRCC1 gene (12) and in the promoter of MDM2 gene (13). Numerous studies have demonstrated the utility of individual and multiple somatic mutation status information in identifying key signaling transduction disruptions. For example, the mutation status of EGFR and KRAS genes can predict the physiological response to certain drugs targeting these molecules (17).

The publication Lin et al. "The grainyhead-like 2 gene (GRHL2) single nucleotide polymorphism is not associated with age-related hearing impairment in Han Chinese", The Laryngoscope, Volume 121, Issue 6, pages 1303-1307, June 2011 pertains to SNPs, but solely in relation to deafness and GRHL2, and does not relate to cancer nor GRHL3.

The publication Van Laer et al. "The grainyhead like 2 gene (GRHL2), alias TFCP2L3, is associated with age-related hearing impairment", Human Molecular Genetics, Volume 17, Issue 2, Pp. 159-169. pertains to SNPs, but solely in relation to deafness and GRHL2, and does not relate to cancer nor GRHL3.

The publication Peters et al. "Mutation of a transcription factor, TFCP2L3, causes progressive autosomal dominant hearing loss, DFNA28", Human Molecular Genetics, Volume 11, Issue 23, Pp. 2877-2885 pertains to SNPs, but solely in relation to deafness and GRHL2, and does not relate to cancer nor GRHL3.

The publication Kamiyama et al. "Polymorphisms in the 3' UTR in the neurocalcin δ gene affect mRNA stability, and confer susceptibility to diabetic nephropathy", Human Genetics, November 2007, Volume 122, Issue 3-4, pp 397-407 pertains to SNPs, but solely in relation to diabetes and GRHL2, and does not relate to cancer nor GRHL3.

The publication Bhandari et al. "The Grainyhead transcription factor Grhl3/Get1 suppresses miR-21 expression and tumorigenesis in skin: modulation of the miR-21 target MSH2 by RNA-binding protein DND1" Oncogene 32, 1497-1507 (21 Mar. 2013) relates to the functional role of GRHL3 in skin cancer but with no reference to SNPs.

The publication Darido et al. "Targeting of the Tumor Suppressor GRHL3 by a miR-21-Dependent Proto-Oncogenic Network Results in PTEN Loss and Tumorigenesis" Cancer Cell, Volume 20, Issue 5, 635-648, 15 Nov. 2011 relates to the functional role of GRHL3 in skin cancer but with no reference to SNPs.

The publication Panis et al. "Putative circulating markers of the early and advanced stages of breast cancer identified by high-resolution label-free proteomics" Cancer Letters Volume 330, Issue 1, Pages 57-66, 1 Mar. 2013 makes mention of GRHL3 in cancer, but relates only to breast cancer, and makes no mention of SNPs.

International application WO2013029116A1 relates to the functional role of GRHL3 in skin cancer, amongst others, but makes no reference to SNPs.

There is thus an extant and urgent need for a solution that allows the end user to indicate patients in a population, who have an increased risk of developing a skin cancer. Unexpectedly, the present invention delivers the solution to such a stated problem.

The object of the present invention is a method for detecting an increased risk of developing skin cancer in human subject characterized in that it comprises A) identifying in a biological sample from the subject the genotypes of at least one homozygotic or heterozygotic single nucleotide polymorphisms (SNPs) in exon 11 Grainyhead-like 3 (GRHL3) gene
at position:
Chr1:24669457, and/or
Chr1:24669459, B) establishing a presence of a genotype leading to an increased risk of developing skin cancer in case of identification at least one of the following genotype:
C→T alteration at position Chr1:24669457, and/or
C→G alteration at position Chr1:24669459.

In one embodiment, the cancer is a non-melanoma skin cancer.

In another embodiment, the cancer is melanoma.

In the method of invention preferably the presence of genotype variant is detected by analysis of DNA, RNA or proteins.

Preferably, the DNA, RNA or protein testing is performed with the use of any methods of identifying homozygotic or heterozygotic SNPs in a genomic, genetic or protein sequence, including Western Blotting with a specific antibody, SNP microarrays, SNP-RFLP, dynamic allele-specific hybridization (DASH), molecular beacons, TAQMAN probes, primer extension (MALDI-TOF mass spectrometry and ELISA-like methods), oligonucleotide ligation assay, single strand conformation polymorphism, temperature gradient gel electrophoresis TGGE, denaturing high performance liquid chromatography, high-resolution melting of the entire amplicon (HRM PCR), SNPlex and/or new generation sequencing (NGS) on tissue or blood sample from a patient, wherein at least one such SNP present at statistically significant levels indicates a dysfunctional downstream system from GRHL3 activity.

Another object of the present invention is a use of the genotype as defined above for in vitro or ex vivo diagnosing an increased risk of developing skin cancer in a human subject.

In the use of genotype defined above, preferably genotype variant of homozygotic or heterozygotic nucleotide polymorphisms (SNPs) associated with skin cancer in the Grainyhead-like 3 (GRHL3) gene or its products is detected by analysis of DNA, RNA or proteins.

The methods are performed preferably on tissue or blood samples from a human subject, wherein at least one such SNP present at statistically significant levels indicates a dysfunctional downstream system from GRHL3 activity.

Preferably, during the use of the invention, DNA, RNA or protein testing is performed with the use of any methods of identifying homozygotic or heterozygotic SNPs in a genomic, genetic or protein sequence, including Western Blotting with a specific antibody, SNP microarrays, SNP-RFLP, dynamic allele-specific hybridization (DASH), molecular beacons, TAQMAN probes, primer extension (MALDI-TOF mass spectrometry and ELISA-like methods), oligonucleotide ligation assay, single strand conformation polymorphism, temperature gradient gel electrophoresis TGGE, denaturing high performance liquid chromatography, high-resolution melting of the entire amplicon (HRM PCR), SNPlex and/or new generation sequencing (NGS) on tissue or blood sample from a patient, wherein at least one such SNP present at statistically significant levels indicates a dysfunctional downstream system from GRHL3 activity.

In one embodiment, the cancer is a non-melanoma skin cancer.

In another embodiment the cancer is melanoma.

DETAILED DESCRIPTION

Figure 2:
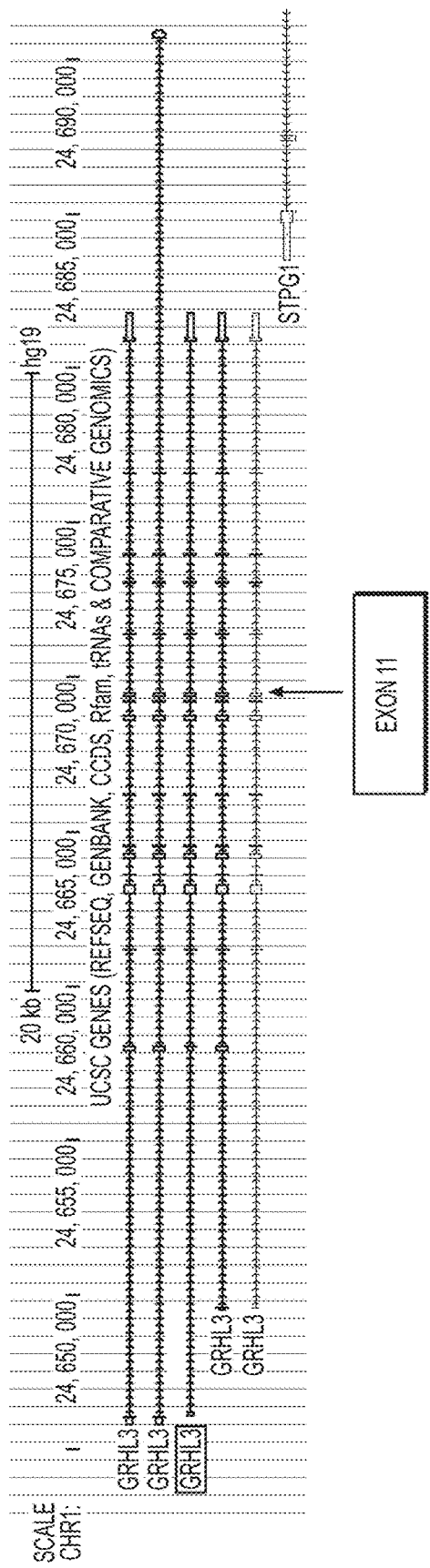
FIG. 2: Alternative splice variants of GRHL.3 mRNA.
Figure 3:
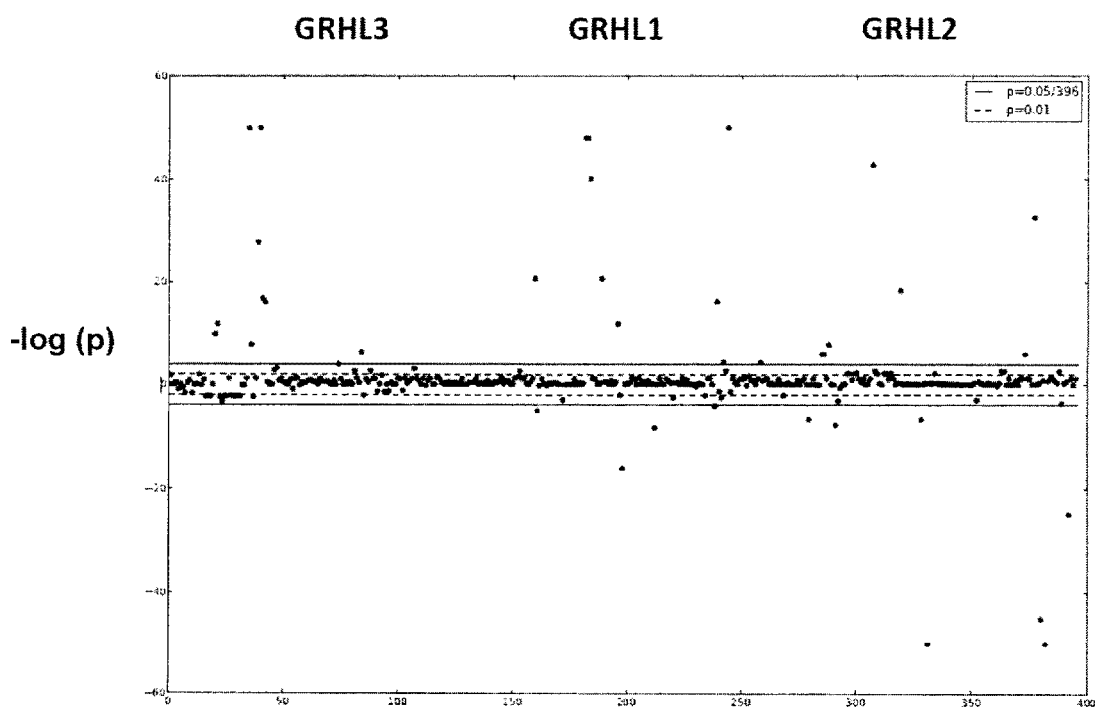
FIG. 3: Manhattan Plot.
Figure 4:
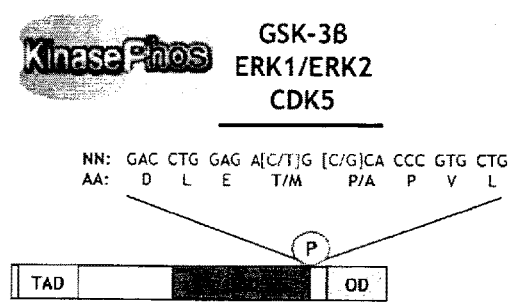
FIG. 4: Location of the potential phorphorylation site in a schematic of the GRHL3 gene; Kinases potentially recognizing the amino-acid motif dependent on SNP1 and SNP2.
Figure 5:
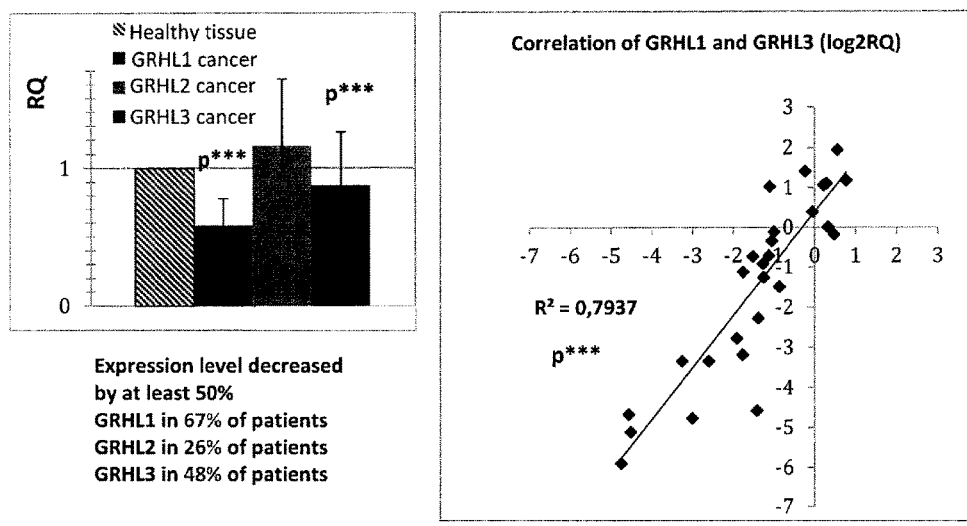
FIG. 5: Changes in the expression level of GRHL genes in patients with non-melanoma skin cancer; correlation of the expression of GRHL1 and GRHL3.

The first aspect of the present invention are SNPs identified in the GRHL3 gene that are skin cancer-specific and lead to loss of function of the GRHL3 protein and therefore likely to the downregulation of PTEN and PI3K/AKT/mTOR pathway activation. In particular, the first aspect of the present invention refers to two SNPs located in exon 11 of GRHL3, which is included in all splice variants of GRHL3, according to the UCSC database. (FIG. 2) (genome.ucsc.edu).

Figure 1:
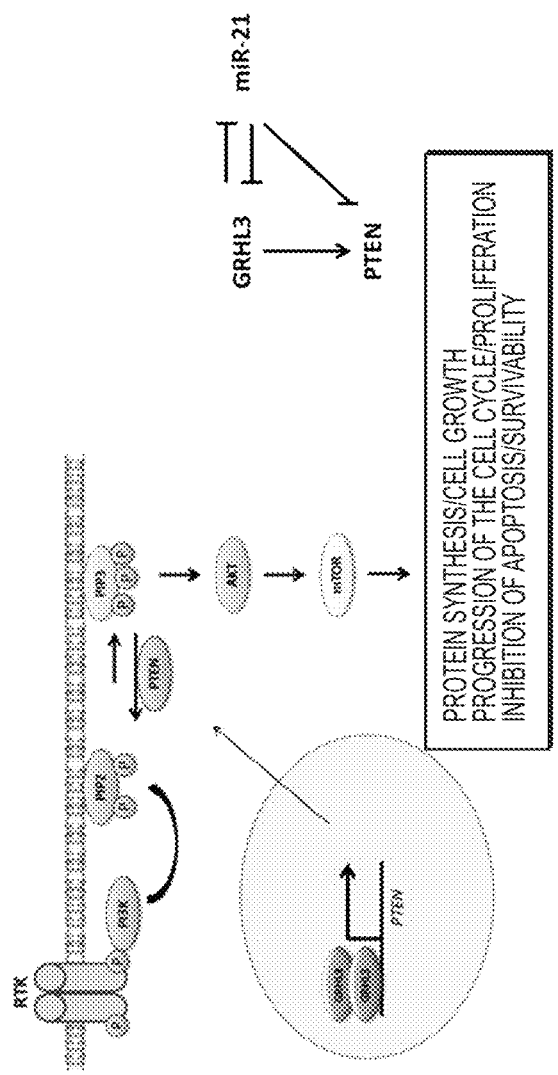
FIG. 1: Pi3K/AKT signaling pathway and the GRHL3/PTEN/miR-231 regulatory loop.

FIG. 1. Splice Variants of mRNA GRHL3.

Moreover, both SNPs are nonsynonymous and result in amino acid variants in the protein and impact the proper function of all isoforms of GRHL3. The first SNP (SNP1, http://www.ncbi.nlm.nih.gov/projects/SNP/snp_ref.cgi?rs=41268753) is a C→T alteration at position 24669457 in exon 11 of GRHL3. The second SNP (SNP2, http://www.ncbi.nlm.nih.gov/projects/SNP/snp_ref.cgi?rs=141193530) is a C→G alteration at position 24669459 in exon 11 of GRHL3.

The second aspect of the present invention is a method of diagnosing an increased risk of developing skin cancer, particularly non-melanoma skin cancer and melanoma, in patients based on the occurrence of at least one of the SNPs according to the present invention. The identification of these SNPs in a patient is used to accurately predict which individuals are susceptible to skin cancer formation.

The third aspect of the present invention is the use of the method of diagnosing an increased risk of developing skin cancer, particularly non-melanoma skin cancer and melanoma, in patients based on the occurrence of at least one of the SNPs according to the present invention in the screening of a human population to detect members susceptible to an increased risk of developing skin cancers.

The fourth aspect of the present invention is the use of the method of diagnosing an increased risk of developing skin cancer, particularly non-melanoma skin cancer and melanoma, in patients based on the occurrence of at least one of the SNPs according to the present invention in clinical prophylaxis programs, especially in populations and locations particularly at risk of developing skin cancers.

The nature of the present invention is illustrated by the following non-limiting examples. A large number of procedural modifications and variants is possible in the course of routine laboratory and research work, which nevertheless do not fall outside of the scope of the present invention.

Example 1

Preparation of Samples for SNP Analysis

Surgical specimens of non-melanoma skin cancers were resected from 32 patients with NMSC and 2 with melanoma (including tumor and adjacent unaffected epidermis) and stored at −80° C. DNA was purified with DNeasy Blood & Tissue Kit (Qiagen). Target enrichment was performed with HaloPlex Kit (Agilent) and targeted fragments of GRHL genes were sequenced with MiSeq Illumina System, 100-fold coverage.

Other possible known methods for detecting the presence of SNPs in the sequence of the GRHL3 gene or its products from biological material isolated from patients include, but are not limited to: Western Blot with Specific Antibody, SNP microarrays, SNP-Restriction Fragment Length Polymorphism (SNP-RFLP), Dynamic allele-specific hybridization (DASH), Molecular beacons, TAQMAN probes, Primer extension (Matrix-assisted laser desorption/ionization-time-of-flight mass spectrometer (MALDI-TOF) and Enzyme-Linked Immunosorbent Assay (ELISA)-like methods), Oligonucleotide Ligation Assay, Single strand conformation polymorphism, Temperature gradient gel electrophoresis (TGGE), Denaturing high performance liquid chromatography, High-resolution melting of the entire amplicon (HRM PCR), SNPlex (Applied Biosystems), New Generation Sequencing (NGS), PCR followed by a restriction digest.

Example 2

Analysis of Allele Frequency and Correlation

Allele frequency in patients group was compared to allele frequency in European population from 1000 Genomes database (a binomial test was used to calculate the p-value).

These two non-synonymous SNPs result in amino acid variants in the protein and may have impact in its proper function. At least one of the SNPs was observed in 9 patients (5 with BCC, 3 with SCC, 1 with Melanoma) as shown in Table 1.

TABLE 1

| Occurrence of SNP alleles and correlation with cancer | | | | | |
|---|---|---|---|---|---|
| | position | Cases (alleles) | exp allele-ratio (1000 Genomes) | obs_allele-ratio | P value |
| chr1 | 24669457 | 3/34 | 0.030 | 0.044118 | 0.460325709845 |
| chr1 | 24669459 | 6/34 | 0.004 | 0.088235 | 0.000000362507395573 |

Both SNPs are of equal merit and a single SNP is sufficient to change protein function. p=4.06238021027e-10 if both SNPs are considered. Two heterozygotic SNPs in coding sequence were identified as overrepresented in the examined population of patients.

Moreover, both amino-acids in whose codons the polymorphisms occur, are found in the motif potentially recognised by such kinases as GSK-3P, ERK1, ERK2 and CDK5 (Rys 4) (kinasephos.mbc.nctu.edu.tw).

The presence of each polymorphism separately brings bout the same effect at the molecular level: the loss of a phosphorylation site of the GRHL3 protein, and thus SNP1 and SNP2 polymorphisms can be treated equally. The likelihood that they occur in a skin cancer patient's skin by accident is thus $p=4.06238021027 \times 10^{-10}$. Another method of representing the above result is the following statement: the probability that the occurrence of either one of the SNPs in a person increases their risk of skin cancer is over 99.99999995%.

The molecular consequences of each of the described single nucleotide polymorphisms, SNP1 and SNP2 in terms of posttranslational modifications and the functioning of the GRHL3 protein are the subject of further research by the authors.

Changes in GRHL Expression Levels in Non-Melanoma Skin Cancers

The GHRL family of transcription factors are an evolutionarily conserved, tissue-specific group of proteins. Their role consists of the transcriptional regulation (activation or repression) of genes significant in the maintenance of the structure and function of epithelia. They control the expression of such genes as DSG1, CDH1, RAB25 and CLDN3 as well as CLDN4, TGM1, PTEN, RhoGEF19, EDC complex genes, hTERT and PCNA and take part in maintaining the equilibrium between proliferation and differentiation of keratinocytes in the epidermis. Disruptions to the GRHL gene expression levels may be directly connected with many skin diseases and/or may be conducive to neoplasm formation.

Example: Changes in the Expression Level of GRHL Gene Expression in Non-Melanoma Skin Cancers RNA was isolated from tumour tissue and healthy tissue collecred from the margin of the sampled changes using a Bio-Gen PRO200 homogenizer and an RNeasy® Fibrous Tissue Mini Kit from Qiagen. Reverse transcription was performed on 250 ng of mRNA using the Superscript® VILO™ Master Mix from Invitrogen. Detection of changes in the expression levels in tumour tissue in relation to healthy tissue in a given patient was evaluated using reagents from Life Technologies: TaqMan® Fast Universal PCR Master Mix (2×) No AmpErase UNG and TaqMan Gene Expression Assays:

| Gene | Assay ID | Exons Included | Amplicon Length |
|---|---|---|---|
| GRHL1 | Hs01119372_m1 | 15-16 | 84 |
| GRHL2 | Hs00227745_m1 | 12-13 | 82 |

-continued

| Gene | Assay ID | Exons Included | Amplicon Length |
|---|---|---|---|
| GRHL3 | Hs00297962_m1 | 14-15 | 99 |
| HPRT | Hs03929098_m1 | 2-3 | 159 |

Real-Time PCR was conducted in a 7900HT Fast Real-Time PCR system from Applied Biosystems. In patients with non-melanoma skin cancers, we observed the decreased expression levels of GRHL1 and GRHL3 as well as correlations between the expression levels of both genes.

Use: The decrease of GRHL expression levels is a molecular marker of skin cancer.

The Effect of Single Nucleotide Polymorphisms on the Level of Expression of GRHL Genes in Non-Melanoma Skin Cancers The regulation of gene expression is a complex process and is dependent on many factors. Moreover, each of the stages of expression can be regulated by different mechanisms. The expression of GRHL genes in the epidermis is dependent on the stage of differentiation of the keratinocyte and on the metabolic and physiological state of the cell.

a) Single Nucleotide Polymorphisms in Regulatory Sequences (Promoters)

Next-generation sequencing of GRHL genes made it possible to indicate single nucleotide polymorphisms in the regulatory regions of GRHL genes in skin cancer patients. Based on the Manhattan Plot analysis prepared (described before) we indicated single nucleotide polymorphisms which may be connected to an increased risk of skin cancer. Changes in the frequency of their occurrence in the evaluated population of patients with non-melanoma skin cancer were statistically significant in comparison to the european population.

TABLE 1

List of SNPs in the promoter sequences of GRHL genes in skin cancer patients

| Chromosome | Gene | Position | rs | Number of patients | Number of alleles | EUR population frequency (1000 Genomes DB) | Frequency in the evaluated population | Direction of frequency change | p Value |
|---|---|---|---|---|---|---|---|---|---|
| chr1 | GRHL3 | 24634151 | rs4648973 | 16 | 20 | 0.170 | 0.286 | + | 0.016 |
| chr1 | GRHL3 | 24635447 | rs72876716 | 6 | 6 | 0.190 | 0.086 | − | 0.022 |
| chr1 | GRHL3 | 24635817 | rs75071937 | 6 | 6 | 0.190 | 0.086 | − | 0.022 |
| chr1 | GRHL3 | 24637441 | rs35621722 | 21 | 27 | 0.250 | 0.386 | + | 0.012 |
| chr1 | GRHL3 | 24638154 | rs942541 | 6 | 6 | 0.220 | 0.086 | − | 0.006 |
| chr1 | GRHL3 | 24638249 | rs591716 | 6 | 6 | 0.220 | 0.086 | − | 0.006 |
| chr1 | GRHL3 | 24638433 | rs592614 | 6 | 6 | 0.220 | 0.086 | − | 0.006 |
| chr1 | GRHL3 | 24639258 | | 6 | 6 | 0.001 | 0.086 | + | 0.000 |
| chr1 | GRHL3 | 24639409 | | 7 | 7 | 0.001 | 0.100 | + | 0.000 |
| chr1 | GRHL3 | 24639413 | rs544030 | 6 | 6 | 0.220 | 0.086 | − | 0.006 |
| chr1 | GRHL3 | 24639724 | rs1769650 | 4 | 4 | 0.210 | 0.057 | − | 0.001 |
| chr1 | GRHL3 | 24639778 | rs1748402 | 6 | 6 | 0.220 | 0.086 | − | 0.006 |
| chr1 | GRHL3 | 24639877 | rs1748401 | 6 | 6 | 0.220 | 0.086 | − | 0.006 |
| chr1 | GRHL3 | 24639932 | rs1769649 | 6 | 6 | 0.210 | 0.086 | − | 0.008 |
| chr1 | GRHL3 | 24640017 | rs620141 | 6 | 6 | 0.220 | 0.086 | − | 0.006 |
| chr1 | GRHL3 | 24640314 | rs621535 | 6 | 6 | 0.220 | 0.086 | − | 0.006 |
| chr1 | GRHL3 | 24640456 | rs622345 | 6 | 6 | 0.220 | 0.086 | − | 0.006 |
| chr1 | GRHL3 | 24640491 | rs478996 | 6 | 6 | 0.220 | 0.086 | − | 0.006 |
| chr1 | GRHL3 | 24641130 | rs2763209 | 26 | 33 | 0.001 | 0.471 | + | 0.000 |
| chr1 | GRHL3 | 24641134 | | 5 | 5 | 0.001 | 0.071 | + | 0.000 |
| chr1 | GRHL3 | 24641138 | rs188840086 | 4 | 4 | 0.180 | 0.057 | − | 0.005 |
| chr1 | GRHL3 | 24641157 | rs55771417 | 14 | 14 | 0.001 | 0.200 | + | 0.000 |
| chr1 | GRHL3 | 24641169 | rs56087219 | 34 | 50 | 0.001 | 0.714 | + | 0.000 |
| chr1 | GRHL3 | 24641177 | rs55927162 | 32 | 48 | 0.210 | 0.686 | + | 0.000 |
| chr1 | GRHL3 | 24641185 | rs56256719 | 33 | 50 | 0.240 | 0.714 | + | 0.000 |
| chr1 | GRHL3 | 24641759 | rs12045977 | 35 | 51 | 0.540 | 0.729 | + | 0.002 |

TABLE 1-continued

List of SNPs in the promoter sequences of GRHL genes in skin cancer patients

| Chromosome | Gene | Position | rs | Number of patients | Number of alleles | EUR population frequency (1000 Genomes DB) | Frequency in the evaluated population | Direction of frequency change | p Value |
|---|---|---|---|---|---|---|---|---|---|
| chr1 | GRHL3 | 24641835 | rs11249086 | 35 | 52 | 0.540 | 0.743 | + | 0.001 |
| chr2 | GRHL1 | 10085631 | rs10929625 | 8 | 8 | 0.220 | 0.114 | − | 0.030 |
| chr2 | GRHL1 | 10086380 | rs1036060 | 35 | 60 | 0.930 | 0.857 | − | 0.030 |
| chr2 | GRHL1 | 10086394 | rs190470103 | 2 | 2 | 0.001 | 0.029 | + | 0.002 |
| chr2 | GRHL1 | 10086398 | rs1036059 | 28 | 39 | 0.680 | 0.557 | − | 0.039 |
| chr2 | GRHL1 | 10086732 | | 10 | 11 | 0.001 | 0.157 | + | 0.000 |
| chr2 | GRHL1 | 10086802 | rs872904 | 3 | 6 | 0.310 | 0.086 | − | 0.000 |
| chr2 | GRHL1 | 10088366 | rs2033324 | 1 | 1 | 0.130 | 0.014 | − | 0.001 |
| chr2 | GRHL1 | 10089843 | | 11 | 22 | 0.001 | 0.314 | + | 0.000 |
| chr2 | GRHL1 | 10089845 | | 11 | 22 | 0.001 | 0.314 | + | 0.000 |
| chr2 | GRHL1 | 10089850 | | 10 | 19 | 0.001 | 0.271 | + | 0.000 |
| chr2 | GRHL1 | 10090435 | | 11 | 11 | 0.001 | 0.157 | + | 0.000 |
| chr2 | GRHL1 | 10091420 | | 7 | 7 | 0.001 | 0.100 | + | 0.000 |
| chr2 | GRHL1 | 10091422 | rs115898376 | 5 | 7 | 0.230 | 0.100 | − | 0.010 |
| chr2 | GRHL1 | 10091472 | rs4630741 | 2 | 4 | 0.520 | 0.057 | − | 0.000 |

Polymorphisms marked with a "+" occur in the patient population more frequently than in the European population, whereas those with a "−" more rarely.

Biological Sense

The presence of single nucleotide polymorphisms in the sequence recognized by transcription factors can lead to the loss, weakening, amplification or creation of a protein binding site or DNA, which leads to changes in the level of gene expression.

b) Single Nucleotide Polymorphisms in the 3'UTR Regions of GRHL Genes

In patients with non-melanoma skin cancer, we observed a simultaneous decrease in the level of gene expression in GRHL3 and GRHL1. The level of expression of both genes in the same time and space may depend on regulation by miRNAs. MicroRNA molecules (miRNAs) regulate the level of gene expression by binding to a specific 7-nucleotide sequence in the 3'UTR of the mRNA molecules. By reducing, the efficiency of translation of genetic information into protein this silences the gene expression level. Upregulation of gene expression levels can be crucial in the process of carcinogenesis. One of the causes of abnormal miRNA/mRNA interaction may be the presence of single nucleotide polymorphisms (SNP) in the sequence encoding the 3'UTR. As a result, this can lead to the elimination of existing or creation of new 6 to 8-nucleotide specific sequences recognized by the miRNA, resulting in an undesirable increase or decrease the level of expression of a given gene.

Next generation sequencing of the GRHL made it possible to indicate single nucleotide polymorphisms in patients with skin cancer in the GRHL gene regions encoding the 3'UTR. On the basis of the indicated Manhattan Plot analysis, we indicate single nucleotide polymorphisms that may be associated with an increased risk of skin cancer. The change in the frequency of their occurrence in a patient population with npn-,elanoma skin cancer was statistically significant in comparison with the European population.

| Chromosome | Gene | Position | rs | Number of patients | Number of alleles | EUR population frequency (1000 Genomes DB) | Frequency in the evaluated population | Direction of frequency change | p Value |
|---|---|---|---|---|---|---|---|---|---|
| chr1 | GRHL3 | 24692283 | rs548942 | 17 | 22 | 0.210 | 0.314 | + | 0.039 |
| chr2 | GRHL1 | 10142073 | rs1052835 | 28 | 39 | 0.420 | 0.557 | + | 0.022 |
| chr2 | GRHL1 | 10143469 | | 3 | 3 | 0.001 | 0.043 | + | 0.000 |
| chr8 | GRHL2 | 102586349 | rs16867839 | 1 | 1 | 0.150 | 0.014 | − | 0.000 |
| chr8 | GRHL2 | 102611707 | rs567029 | 1 | 2 | 0.610 | 0.029 | − | 0.000 |
| chr8 | GRHL2 | 102681482 | rs7820879 | 13 | 13 | 0.001 | 0.186 | + | 0.000 |
| chr8 | GRHL2 | 102681820 | rs201378138 | 4 | 4 | 0.001 | 0.057 | + | 0.000 |

The presence of single nucleotide polymorphisms in the recognition sequence of the miRNA may lead to the loss, weakening, amplification or creation of a binding site for miRNA/mRNA. The effect of single nucleotide polymorphisms in GRHL genes was determined using two databases: PolymiRTS 3.0 and MirSNP. One of the single nucleotide polymorphisms: rs1052835 deserves special attention. It is found in the 3'UTR of the GRHL1 gene in patients with non-melanoma skin cancer much more frequently than in the European population, moreover, occurs most frequently in homozygous form. Substitution of a single nucleotide causes the creation of an additional complementary base pair in the recognition sequence of hsa-miR-802, which reinforces the bond strength of miRNA/mRNA. According the Miro base (http://ferrolab.dmi.unict.it/index.html), hsa-miR-802 is present in nonmelanoma skin cancers, and its target genes include PTCH1 (SHH receptor suppressor of tumorigenesis), PTGS2, GSTM3. Interestingly, the sonic hedgehog pathway is critical in the development of non-melanoma skin cancers (sample publications: http://www.ncbi.nlm.nih.gov/pubmed/17988327, http://www.ncbi.nlm.nih.gov/PubMed/20848446.). The transcription factor GRHL1 shows (like PTCH1) tumour suppressor activity (work by Michał Mlącki). miR-802 can regulate both genes and exhibit oncogenic activity in the context of the development of skin cancer. The presence of SNPs in the recognition sequence of miR-802 can lead to excessive GRHL1 gene repression.

```
                    Sequence list

Sequence ID 1
SNP1 -
www.ncbi.nlm.nih.gov/projects/SNP/snp_ref.cgi?rs =
41268753
Chr 1: 24669457, C → T rs41268753:
CCTTCGGCCAGAGACTGACCTGGAGA[C/T]GCCACCCGTGCTGTTCATC
CCCAATGT Sequence ID 2
SNP2 -
www.ncbi.nlm.nih.gov/projects/SNP/snp_ref.cgi?rs =
141193530
Chr 1: 24669459, C → G rs141193530:
CCTTCGGCCAGAGACTGACCTGGAGACG[C/G]CACCCGTGCTGTTCATC
CCCAATGT
```

Robinson, J K. Sun exposure, sun protection, and vitamin D. *JAMA* 2005; 294:1541-43.

Rogers, H W, Weinstock, M A, Harris, A R, et al. Incidence estimate of nonmelanoma skin cancer in the United States, 2006. *Arch Dermatol* 2010; 146(3):283-287.

Koh H K, Geller A C, Miller D R, Grossbart T A, Lew R A. Prevention and early detection strategies for melanoma and skin cancer: Current status. Archives of Dermatology. 1996; 132: 436-442 www.ncbi.nlm.nih.gov/pubmed/18173697 archderm.jamanetwork.com/article.aspx?articleid=480781 www.medscape.org/viewarticle/727252_3 www.ncbi.nlm.nih.gov/pubmed/20465691 www.who.int/uv/publications/solaradabd/en/index.html www.nature.com/onc/journal/v32/n12/pdf/onc2012168a www.ncbi.nlm.nih.gov/pubmed/10517972 www.nature.com/bjc/journal/v91/n8/abs/6602174a link.sprinaer.com/article/10.1007/s10552-008-9231-9

American Cancer Society. Cancer Facts & Figures 2013. www.cancer.org/acs/groups/content/@epidemiologysurveilance/documents/document/acspc-036845. Accessed Jan. 31, 2013.

www.ncbi.nlm.nih.gov/pubmed/22453015 www.sciencedirect.com/science/article/pii/S1535610811003977 informahealthcare.com/doi/abs/10.3109/00016480802620662

SEQUENCE LISTING

```
<160> NUMBER OF SEQ ID NOS: 2

<210> SEQ ID NO 1
<211> LENGTH: 54
<212> TYPE: DNA
<213> ORGANISM: homo sapiens
<220> FEATURE:
<221> NAME/KEY: mutation
<222> LOCATION: (27)..(27)
<223> OTHER INFORMATION: y is C or T

<400> SEQUENCE: 1
ccttcggcca gagactgacc tggagaygcc acccgtgctg ttcatcccca atgt        54

<210> SEQ ID NO 2
<211> LENGTH: 54
<212> TYPE: DNA
<213> ORGANISM: homo sapiens
<220> FEATURE:
<221> NAME/KEY: mutation
<222> LOCATION: (29)..(29)
<223> OTHER INFORMATION: y is C or G

<400> SEQUENCE: 2
ccttcggcca gagactgacc tggagacgyc acccgtgctg ttcatcccca atgt        54
```

BIBLIOGRAPHIC REFERENCES

Stern, R S. Prevalence of a history of skin cancer in 2007: results of an incidence-based model. *Arch Dermatol* 2010; 146(3):279-282.

The invention claimed is:

1. A method for detecting a Grainyhead-like 3 (GRHL3) single nucleotide polymorphism in a human subject, comprising:

a) obtaining a tissue or blood sample from a human subject that comprises subject nucleic acid; and b) detecting in the subject nucleic acid the single nucleotide polymorphism (SNP) C→T at position Chr1:24669457 and/or the single nucleotide polymorphism C→G at position Chr1:24669459.

2. The method of claim 1, wherein at least one of the detected SNP(s) is heterozygous.

3. The method of claim 1, wherein at least one of the detected SNP(s) is homozygous.

4. The method of claim 3, wherein the human subject has melanoma skin cancer.

5. The method of claim 1, wherein the SNP C→T at position Chr1:24669457 is detected.

6. The method of claim 5, wherein the human subject has non-melanoma skin cancer.

7. The method of claim 1, wherein the SNP C→G at position Chr1:24669459.

8. The method of claim 7, wherein the human subject has non-melanoma skin cancer.

9. The method of claim 7, wherein the human subject has melanoma skin cancer.

10. The method of claim 1, wherein the SNP C→T at position Chr1:24669457 is detected and the SNP C→G at position Chr1:24669459 is detected.

11. The method of claim 10, wherein the human subject has non-melanoma skin cancer.

12. The method of claim 10, wherein the human subject has melanoma skin cancer.

13. The method of claim 1, wherein the SNP C→T at position Chr1:24669457 and/or the SNP C→G at position Chr1:24669459 is detected in DNA in the subject sample.

14. The method of claim 1, wherein the SNP C→T at position Chr1:24669457 and/or the SNP C→G at position Chr1:24669459 is detected in RNA in the subject sample.

15. The method of claim 1, wherein the subject sample is a blood sample.

16. The method of claim 1, wherein the subject sample is a surgical specimen.

* * * * *